(12) United States Patent
Berger et al.

(10) Patent No.: US 6,767,854 B2
(45) Date of Patent: Jul. 27, 2004

(54) GLASSY-CRYSTALLINE MATERIAL WITH LOW SOLUBILITY AND PROCESS OF PREPARING THE SAME

(75) Inventors: Georg Berger, Zepernick (DE); Ute Ploska, Berlin (DE)

(73) Assignee: Bam Bundesanstalt fuer Materialforschung und Prufung (DE)

(*) Notice: Subject to any disclaimer, the term of this patent is extended or adjusted under 35 U.S.C. 154(b) by 13 days.

(21) Appl. No.: 10/170,779

(22) Filed: Jun. 13, 2002

(65) Prior Publication Data

US 2002/0193230 A1 Dec. 19, 2002

(30) Foreign Application Priority Data

Jun. 15, 2001 (DE) .......................... 101 29 844
May 17, 2002 (DE) .......................... 102 23 102

(51) Int. Cl.[7] .......................... C03C 10/02; C03C 1/00; C03C 3/247; C03C 10/16
(52) U.S. Cl. .......................... 501/10; 501/1; 501/32; 501/102; 501/44; 501/46; 65/33.3
(58) Field of Search .......................... 501/1, 10, 32, 501/44–46, 102; 65/33.3

(56) References Cited

U.S. PATENT DOCUMENTS 4,376,168 A * 3/1983 Takami et al. .................. 501/1
4,871,384 A * 10/1989 Kasuga ........................ 65/30.1

FOREIGN PATENT DOCUMENTS

JP 62268561 A * 11/1987 .......... A61L/27/00

OTHER PUBLICATIONS

Derwent Abstract 1988–004048 of JP 62–268561A.*
Berger, et al., "Hydroxyapatite's Solubility May Cause Loosening of Coated Implants", Key Engineering Materials vols. 192–195 (2001) pp. 111–114.
Berger, et al., "Long–Term Stable Bioactive Glass Ceramics as Implant Material—Ten Years of Clinical Experience", Fourth World Biomaterials Congress, Apr. 24–28, 1992.
Kukubo, Tadashi; "Bioactive glass ceramics: properties and applications", Biomaterials 1991, vol. 12 Mar.
Ploska, et al., "Solubility of compositions in the system CaTixZr4–x(PO4)6 with x=0–4", Biomaterials 1997, vol. 18, No. 24.
Berger, et al., "Clinical Application of Surface Reactive Apatite/Wollastonite Containing Glass–Ceramics", XV. Int. Congress on Glass, Leningrad, USSR, 3,–7.7. 1989, vol. 3a, pp. 120–136.

* cited by examiner

Primary Examiner—Karl Group
Assistant Examiner—Elizabeth A. Bolden
(74) Attorney, Agent, or Firm—Pendorf & Cutlitf

(57) ABSTRACT

The invention refers to a material which is chemically long-term stable in a neutral or slightly acid environment and which can be used both as bioactive bone replacement material, e.g. in the form of a coating applied onto metallic prosthesis sticks by thermal spraying, and as substrate material in biotechnology, e.g. in the form of a ceramic sheet. According to the invention, said material comprises 15–45% by weight CaO, 40–45% by weight $P_2O_5$, 10–40% by weight $ZrO_2$ and fluoride, said material further comprises two crystalline phases being apatite and calcium zirconium phosphate, and a secondary glass phase. Said material has a very high chemical long-term stability, compared to known materials which can also be produced by means of a melting process.

14 Claims, 1 Drawing Sheet

FIG. 1   X-ray diffraction diagram of composition code: Apatite/CZP1
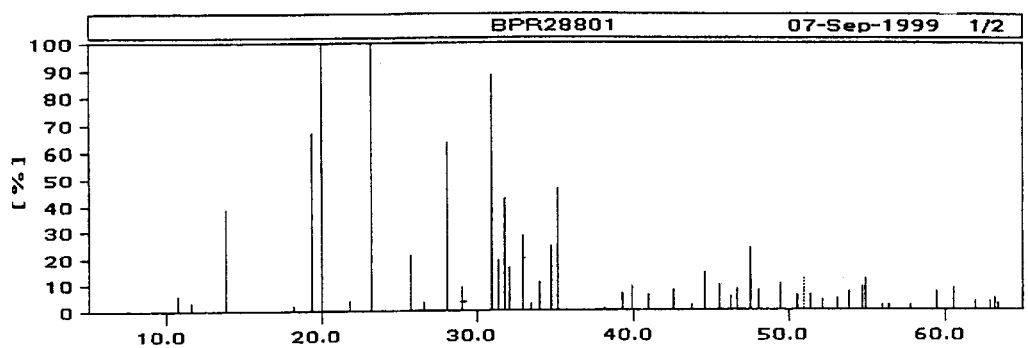
FIG. 2   X-ray diffraction diagram of composition code: Apatite/CZP2
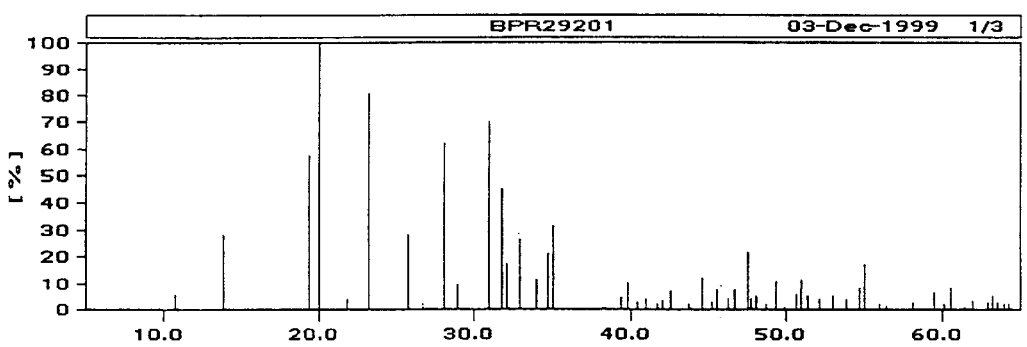

US 6,767,854 B2

GLASSY-CRYSTALLINE MATERIAL WITH LOW SOLUBILITY AND PROCESS OF PREPARING THE SAME

BACKGROUND OF THE INVENTION

1. Field of the Invention

The invention refers to a glassy-crystalline material with low solubility which can be used both as bioactive bone replacement material, e.g. in the form of a coating applied onto metallic prosthesis sticks by thermal spraying, and as substrate material in biotechnology, e.g. in the form of a ceramic sheet or body. The invention also refers to a manufacturing method.

2. Description of the Related Art

In principal, long-term stable inorganic materials are known. Materials that are specifically used as bioactive bone replacement materials and have a sufficient long-term stability have also been described in the relevant literature. For example, there have been continuous publications dedicated to the successful clinical use of glass ceramics and sintered glass ceramics the main crystal phases of which are apatite and wollastonite [Kokubo, T., Biomaterials, 12 (1991) 155–163; Berger, G. et al.: Long-term stable bioactive glass ceramics as implant material—ten years of clinical experience, Fourth World Biomaterial Congress, Berlin, Apr. 24–28, 1992, Transactions p. 33]. The chemical stability of the aforesaid materials has been surpassed by that of other bioactive materials on the basis of calcium-zirconium/titanium phosphate (Biomaterials 18 (1997) 1671–1675) which can only be manufactured using ceramic methods, but do not melt at temperatures which are common in the glass industry (approximately 1650° C.), which is known to cause disadvantages as regards the mechanical stability of such granulated materials and particularly of bodies manufactured thereof.

The object of the invention is to provide a glassy-crystalline material, which enables bones to be directly joined with no connective tissue in between and which at the same time is long-term stable.

SUMMARY OF THE INVENTION

According to the invention, the glassy-crystalline material on the basis of CaO, $P_2O_5$, $ZrO_2$ and fluoride consists of 15–45% by weight CaO, 40–45% by weight $P_2O_5$, 10–40% by weight $ZrO_2$ and 0.7–3.5% by weight of fluoride and contains apatite and calcium zirconium phosphate as main crystal phases and a glass phase as secondary component, the main crystal phases jointly making up at least 35% by weight and the secondary components making up 5 to 15% by weight, and all percentages being relative to the total weight of the glassy-crystalline material.

BRIEF DESCRIPTION OF THE DRAWINGS

In the following the invention will be described in greater detail on the basis of an embodiment schematically represented in the figures. There is shown FIG. 1 shows an X-ray diffraction diagram of the material according to Example 1.

FIG. 2 shows an X-ray diffraction diagram of the material according to Example 2.

DETAILED DESCRIPTION OF THE INVENTION

A preferred glassy-crystalline material contains 23–39% by weight CaO, 40–45% by weight $P_2O_5$, 20–35% by weight $ZrO_2$ and 1–3% by weight of fluoride and contains apatite and calcium zirconium phosphate as main crystal phases and a glass phase as secondary component, the main crystal phases jointly making up at least 35% by weight and the secondary components making up 5 to 15% by weight.

Another preferred glassy-crystalline material contains 20–35% by weight CaO, 40–45% by weight $P_2O_5$, 20–35% by weight $ZrO_2$ and 1–3% by weight of fluoride and in addition 0.1 to 6% by weight $Na_2O$ and contains apatite and calcium zirconium phosphate as main crystal phases and a glass phase as secondary component and in addition a sodium zirconium phosphate phase as secondary component. In this material, the main crystal phases jointly make up at least 35% by weight and the secondary components can make up 5 to 15% by weight each.

Further, the glassy-crystalline material according to the invention can additionally contain 0.1 to 6% by weight of magnesium oxide and/or potassium oxide and, if so, the corresponding phases as secondary components.

The $Na_2O$, MgO and/or $K_2O$ content is preferably in the range of 1 to 6% by weight. The content of the corresponding sodium zirconium phosphate secondary crystal phase is preferably in the range of 5 to 10% by weight.

In an advantageous embodiment, up to 15% by weight of a ground glass can be added to the mixture to be melted, which ground glass consists of $SiO_2$, $Al_2O_3$ and MgO and in some cases CaO and the composition and characteristics of which correspond to those of a cordierite glass, which considerably improves the sintering activity of the glassy-crystalline material according to the invention. Such an added glass has a particularly high melting point (>1500° C.) and is chemically stable as regards the influence of water, acids and alkaline solutions.

The terms "glass ceramics" and "glassy-crystalline material" used herein cannot always be clearly defined. Both crystalline and glassy or X-ray amorphous phases are present in a thoroughly mixed state. It is of no importance for the present invention whether one phase is located adjacent to the other or one phase encloses the other. The term "main crystal phase" refers to a crystalline phase, which is contained in at least twice the amount of a secondary phase, concentrations of approximately 15% by weight and below, preferably below 10% by weight, being referred to as secondary phases.

Surprisingly, the solubility of the material has been found to be very low, even in a slightly acid medium as observed in the case of inflammatory reactions, i.e. pH=6.0, although the said material contains apatite [Berger et al., Hydroxyapatite's solubility may cause loosening of coated implants, Bioceramics Vol. 13, edited by Santro Giannini and Antonio Moroni (Proceedings of the 13th International Symposium on Ceramics in Medicine); Trans Tech Publ. Ltd, Swiss, 2000, 111–114].

Further, it has surprisingly been found that, after an initial alkaline reaction, the surface properties of the material (the glassy-crystalline material) change towards physiological pH values (7.4) if the said material is stored in deionized water, due to which it is of interest to biotechnology.

In addition, the material according to the invention could not be expected to surprisingly be processable into slurries, which are suitable for manufacturing spongiosa-like bodies and ceramic sheets since there are numerous examples of known materials in the relevant literature, which do not have these characteristics.

The thermal coefficient of expansion of the new material is in the range of 1.4 and $6 \times 10^{-6}$ degrees$^{-1}$ between 27° C. and 300, 400, 600 or 800° C. It is in the range of 1.4 and $8 \times 10^{-6}$ degrees$^{-1}$ between 27° C. and 300, 400, 600 and 800° C. if the manufacturing process of the material includes holding stages during the cooling down of the melted mass, as described below.

Another characteristic feature of the material consists in that it has a total solubility of 4 to 5.5 mg/l if the test is carried out in a 0.2 M TRIS HCl buffer solution at pH=7.4, T=37° C., using a grain size fraction of 315–400 ìm, the duration of the test being 120 h and the ratio of surface area (sample) to volume (solvent) being 5 cm$^{-1}$.

Another characteristic feature of the material consists in that even storage in water (144 h) at 37° C. causes the surface of the material to change so that physiological pH values of approximately 7.4 can be measured. If the temperature of the water bath is increased, the change of the surface properties is accelerated accordingly.

Glass ceramics having the following characteristics can be obtained if the manufacturing process of the material according to the invention includes one or two holding stages during the cooling down of the melted mass in the furnace between 800 and 1100° C., as in a further embodiment described below:

- a total solubility of 0.2 to 2.0 mg/l if the test is carried out in a 0.2 M TRIS HCl buffer solution at pH=7.4, T=37° C., using a grain size fraction of 315–400 μm, the duration of the test being 120 h and the ratio of surface area (sample) to volume (solvent) being 5 cm$^{-1}$,
- a thermal coefficient of expansion between 1.4 and 8×10$^{-6}$ degrees$^{-1}$ between 27° C. and 300, 400, 600 and 800° C.,
- stability in the pH range between 7.0 and 7.5.

The chemical stability of such a material is therefore 3 to 10 times higher than that of a material manufactured without holding stages since the total solubility is in the range of 0.2 to 2.0 mg/l.

According to the invention, the material is manufactured by combining the substances which are suitable for forming the mixture, i.e. 15–45% by weight CaO, 40–45% by weight $P_2O_5$, 10–40% by weight $ZrO_2$ and 0.7–3.5% by weight of fluoride, and melting them at 1550 to 1650° C. using suitable, usually multistage thermal treatment programs (holding stages in the range of 400 to 1500° C.) and a suitable crucible material, e.g. consisting of a Pt/Rh alloy. The melted mass is poured out and once the mass has solidified it is cooled down to room temperature in air (spontaneous cooling) or in a cooling furnace, depending upon its intended use, the cooling process including holding stages if appropriate.

Holding stages in thermal treatment program of about each at 400, 800 and 1000° C. can be added to improve the reproducibility of the melting reaction.

Advantageously, the fluoride is added in the form of $CaF_2$ and in concentrations of 1.5–7% by weight. Alternatively, it can also be added in the form of $ZrF_2$ or, as the case may be, NaF, KF or $MgF_2$.

In another embodiment, the method is characterized in that the said mixture of 15–45% by weight CaO, 40–45% by weight $P_2O_5$, 10–40% by weight $ZrO_2$ and 0.7–3.5% by weight of fluoride is melted at 1550 to 1650° C., the melting process including several holding stages in the range of 400 to 1500° C., and is then cooled down in the furnace in a controlled manner and at a rate of 60° C./h to 300° C./h, the cooling process lasting for 2 to 10 h and including two holding stages, one holding stage between 1000 and 1100° C. and another one between 800 and 1000° C.

Once the material has been cooled down it is e.g. ground, mixed with commonly used sintering aids and pressed into bodies in order to obtain a densely fired ceramic body after sintering.

Alternatively, the material manufactured according to the invention can e.g. be ground, mixed with commonly used sintering aids and processed into a slurry which is then applied onto a polyurethane sponge and sintered in several sintering stages at such high temperatures that the polyurethane sponge and the sintering aids are burnt completely and a spongiosa-like body is obtained the main crystalline components of which are apatite and calcium zirconium phosphate.

Another processing option consists in grinding the material, adding commonly used sintering aids and processing the slurry obtained in this way into a sheet which has an open-pore structure once the firing process has finished.

Another object of the invention consists in the use of the glassy-crystalline material according to the invention for the manufacture of granulated materials, ceramic bodies or ceramic sheets having a dense or open-pore structure.

The invention will hereinafter be explained in detail by way of examples. All percentages are by weight if not indicated otherwise.

EXAMPLES

Example 1

A mixture is prepared the composition of which is as follows (code: Apatite/CZP1):
25.88 CaO
28.44 $ZrO_2$
43.68 $P_2O_5$
5.00 $CaF_2$ It is practicable to add the CaO portion in the form of 62.79 $CaHPO_4$ and the $P_2O_5$ portion required in the form of 10.51 ml of a 85% $H_3PO_4$. First, $CaHPO_4$, $ZrO_2$ and $CaF_2$ are thoroughly mixed, subsequently the phosphoric acid is added and the reaction product is ground in a mortar and put into a drying chamber, the drying process including temperature holding stages lasting for a total of 4 h in the range of 120° C. to 170° C. The reaction mixture obtained is taken out and filled into a Pt/Rh crucible and is heated, cooled down and ground in a mortar, the heating process including 1 h holding stages at 400 and 800° C. The material pretreated in this way is now melted in a Pt/Rh crucible, the melting process including 15 min holding stages at 800, 1000, 1300, 1500 and finally 1600° C., and subsequently poured onto a steel plate (room temperature).

Part of the solidified mass was pulverized by grinding it in an agate mill, particles below 43 μm were separated by sieving and subsequently subjected to an X-ray diffraction analysis. The result (cf. FIG. 1) shows that the crystal phases apatite (fluorapatite/hydroxylapatite) and calcium zirconium phosphate [$CaZr_4(PO_4)_6$] are clearly detectable.

Example 2

A mixture according to the instructions of Example 1 is prepared except that sodium oxide is added as additional component (code: Apatite/CZP2). In this approach, the mixture is to be composed as follows:
59.93 $CaHPO_4$
27.10 $ZrO_2$
3.42 $Na_2O$
5.00 $CaF_2$ and
9.56 ml of a 85% $H_3PO_4$ acid.

Processing was done as in Example 1. Following the last temperature holding stage, the melted mass was poured out of the crucible onto a steel plate.

Part of the solidified mass was pulverized by grinding it in an agate mill, particles below 43 ìm were separated by sieving and subsequently subjected to an X-ray diffraction analysis. The result (cf. FIG. 2) shows that the crystal phases apatite (fluorapatite/hydroxylapatite) and calcium zirconium phosphate [$CaZr_4(PO_4)_6$] and sodium zirconium phosphate [$NaZr_2(PO_4)_3$] are detectable in the glassy-crystalline material.

Example 3

A glassy-crystalline material according to Example 1 (Apatite/CZP1) is produced. The material is pulverized by grinding it in a mill lined with zirconium oxide so that a $D_{50}$ value of 8 mm is obtained. The ground material is mixed with a 5% polyvinyl alcohol (PVA) solution, the ratio of ground material to PVA solution being 90:10% by weight, and pressed into a stick at 4.7 kN in a stamping press. This green compact is sintered at a temperature of 1050° C.

Subsequently, the thermal coefficient of expansion (CE) of the relatively dense body obtained in this way is determined:

CE in the range of 27–400° C.: $1.90 \times 10^{-6}$ degrees Celsius$^{-1}$
CE in the range of 50–400° C.: $1.86 \times 10^{-6}$ degrees Celsius$^{-1}$
CE in the range of 30–300° C.: $1.45 \times 10^{-6}$ degrees Celsius$^{-1}$
CE in the range of 30–400° C.: $1.88 \times 10^{-6}$ degrees Celsius$^{-1}$
CE in the range of 30–600° C.: $2.6 \times 10^{-6}$ degrees Celsius$^{-1}$
CE in the range of 30–800° C.: $3.2 \times 10^{-6}$ degrees Celsius$^{-1}$

Example 4

A glassy-crystalline material according to Example 1 (Apatite/CZP1) is produced. Subsequently, the material is ground in a mortar and a grain size fraction of 315–400 μm produced.

The granulated material obtained in this way is compared with a basic glass ($Ap40_{glass}$) and an apatite and wollastonite-based glass ceramic material produced from this basic glass ($Ap40_{cryst.}$) [i.e. chemical composition as follows (% by weight): 44.3 $SiO_2$; 11.3 $P_2O_5$; 31.9 CaO; 4.6 $Na_2O$; 0.19 $K_2O$; 2.82 MgO and 4.99 $CaF_2$, manufactured according to patent DD 247 574] as regards chemical stability.

First, the specific surface areas were determined according to BET using krypton as measuring gas:
Apatite/CZP1: 0.364 m$^2$/g
$Ap40_{glass}$: 0.018 m$^2$/g
$Ap40_{cryst.}$: 0.055 m$^2$/g.

It can be seen that the material according to the invention has a certain open porosity compared to the basic glass and the glass ceramic material produced therefrom. In the solubility tests, these differences are taken into account in that the ratio of surface area (samples) to volume of solvent (TRIS HCl buffer solution) is adjusted to 5 cm$^{-1}$ in all cases.

A 0.2 M TRIS HCl buffer solution whose pH=7.4 at 37° C. was used as solvent. The samples were stored therein at 37° C. for a period of 120 h. Subsequently, the total solubility was determined by determining the individual ions (Ca, P, Zr) in the solution by means of an ICP measurement:
Apatite/CZP1: 4.1–5.1 mg/l
$Ap40_{glass}$: 318–320 mg/l
$Ap40_{cryst.}$: 75.2–82.0 mg/l.

These values impressively prove the high chemical stability of the material according to the invention under simulated physiological conditions, a known method for the in vitro determination of long-term stability.

Example 5

Processing is done as in Example 4, except that a 0.2 M TRIS HCl buffer solution whose pH value is 6.0 at 37° C. is used for measuring. In this way, it this possible to simulate a pH drop from the physiological 7.4 value down into the acid range due to an infection during wound healing or at a later stage.

The following total solubility values (Ca, P, Zr) were determined by means of ICP:
Apatite/CZP1: 16–19 mg/l
$Ap40_{glass}$: 505–518 mg/l
$Ap40_{cryst.}$: 117–125 mg/l.

These values impressively prove the high chemical stability of the material according to the invention under simulated conditions, as they are present during an inflammatory reaction. According to the values measured, the increase of the absolute solubility values of the material according to the invention is much smaller than the rather dramatic increase which has been determined for the basic glass and the apatite/wollastonite-based glass ceramic material.

Example 6

A glassy-crystalline material according to Example 2 (Apatite/CZP2) is produced. The material is pulverized by grinding it in a mill lined with zirconium oxide so that a $D_{50}$ value of 8 μm is obtained. 100 g of this ground material is mixed with 45 g of a mixture consisting of 90% by weight of polyethylene glycol and 10% by weight of a commercially available surface-active agent and with 5 ml isopropyl alcohol so that a slurry is obtained. This slurry is applied onto open-pore PUR sponges whose porosity is between 80 and 20 ppi (pores per inch) by repeatedly immersing and squeezing the sponges, dried overnight in a drying chamber at 120° C. and subsequently heated slowly up to 1050° C. at a rate of 1° C. per minute. The result is a spongiosa-like material the structure of which resembles that of the sponge used while the PUR sponge has burnt completely.

Example 7

A glassy-crystalline material according to Example 1 (Apatite/CZP1) is produced. The material is pulverized by grinding it in a mill lined with zirconium oxide so that a $D_{50}$ value of 8 μm is obtained. 1 g of this freshly ground material is added to 100 ml of a deionized water according to ISO 3696 and the pH value change measured over a period of 144 h.

Surprisingly it was found that the pH value of 8.8, which was determined after the material, had been stored in deionized water for one hour decreases to the physiological value of 7.4 after 144 h, due to which the said material becomes interesting to biotechnology, in particular.

Example 8

A mixture according to the instructions of Example 1 is prepared except that the following component composition was selected (code: Apatite/CZP3):
80.79 g $CaHPO_4$
19.42 g $ZrO_2$
4.87 g $CaF_2$ and
0.62 ml of a 85% phosphoric acid.

Processing was done as in Example 1 except that the melted mass was not poured onto a steel plate, but cooled down in a defined manner in the furnace, the cooling process including two holding stages at 1050° C. (6 h) and 950° C. (6 h). The total solubility of this material is 0.81 mg/l if the test is carried out in a 0.2 M TRIS HCl buffer solution at pH=7.4, T=37° C., using a grain size fraction of 315–400 μm, the duration of the test being 120 h and the ratio of surface area (sample) to volume (solvent) being 5 cm$^{-1}$.

Example 9

A mixture according to the instructions of Example 8 (Apatite/CZP3) is prepared, the component composition used being as follows:
37.38% by weight CaO
14.45% by weight $ZrO_2$
42.64% by weight $P_2O_5$
5.53% by weight $CaF_2$ Further, 10% by weight of a ground glass ($D_{50}$=4.6 mm) composed as follows:
12.05% by weight MgO
1.00% by weight CaO
38.00% by weight $Al_2O_3$
48.95% by weight $SiO_2$
was added to the aforesaid sintered and ground material in order to improve its sintering activity.

Subsequently, the said materials mixture was processed according to Example 6 except that tempering was carried out as follows:

A PUR sponge onto which the slurry had been applied was heated up to 1300° C. at a rate of 700° C./h, the result obtained being a spongiosa-like body.

What is claimed is:

1. A glassy-crystalline material with low solubility comprising CaO, $P_2O_5$, $ZrO_2$ and fluoride, wherein the amount of CaO is 15–45% by weight, $P_2O_5$ is 40–45% by weight, $ZrO_2$ is 10–40% by weight, and fluoride is 0.7–3.5% by weight, said material comprises apatite and calcium zirconium phosphate as main crystal phases and a glass phase as a secondary component, the combined amount of said main crystal phases is at least 35% by weight and said combined amount of said secondary components is 5 to 15% by total weight of said glassy-crystalline material.

2. The material according to claim 1, wherein said material contains 23–39% by weight CaO, 40–45% by weight $P_2O_5$, 20–35% by weight $ZrO_2$ and 1–3% by weight of fluoride.

3. The material according to claim 1, wherein said material additionally contains 0.1 to 6% by weight of at least one of $Na_2O$, MgO and $K_2O$ and their corresponding phases as an additional secondary component.

4. The material according to claim 1, wherein said material additionally contains a sodium zirconium phosphate phase.

5. The material according to claim 1, wherein said material is present in the form selected from the group consisting of a granulated material, a ceramically processed dense body, a ceramically processed porous body and a ceramic sheet.

6. The material according to claim 1, wherein said material satisfies at least one of the following parameters:
 a total solubility of 0.2 to 5.5 mg/l if the test is carried out in a 0.2 M TRIS HCl buffer solution at pH=7.4, T=37° C., using a grain size fraction of 315–400 mm, the duration of the test being 120 h and the ratio of surface area (sample) to volume (solvent) being 5 $cm^{-1}$,
 a thermal coefficient of expansion between 1.4 and $8 \times 10^{-6}$ $degrees^{-1}$ between 27° C. and 300, 400, 600 and 800° C., and
 stability in the pH range between 7.0 and 7.5.

7. A method for manufacturing a glassy-crystalline material according to claim 1, wherein a mixture of 15–45% by weight CaO, 40–45% by weight $P_2O_5$, 10–40% by weight $ZrO_2$ and 0.7–3.5% by weight of fluoride is melted at 1550 to 1650° C. wherein the melting process includes at least one holding stage in the range of 400 to 1500° C., and said glassy-crystalline material is obtained in the form of a melted mass which is cooled down spontaneously or step by step.

8. The method according to claim 7, wherein 0.1 to 3% by weight of at least one of $Na_2O$, MgO and $K_2O$ is added to said mixture.

9. The method according to claim 7, wherein up to 15% by weight of a ground glass are added, said glass comprising $SiO_2$, $Al_2O_3$ and MgO, and the composition and characteristics of said glass correspond to those of a cordierite glass.

10. The method according to claim 9, wherein said added ground glass further comprises CaO.

11. The method according to claim 7, wherein said method comprises melting of a mixture of 15–45% by weight CaO, 40–45% by weight $P_2O_5$, 10–40% by weight $ZrO_2$ and 0.7–3.5% by weight of fluoride at 1550 to 1650° C., said melting process includes at least one holding stage in the range of 400 to 1500° C., and one cooling stage, said cooling stage comprises cooling down said mixture in the furnace in a controlled manner and at a rate of 60° C./h to 300° C./h, said cooling process lasts 2 to 10 h and includes a first holding stage between 1000 and 1100° C. and a second holding stage between 800 and 1000° C.

12. A method for manufacturing granulated material, wherein said method comprises
 (i) grinding the glassy-crystalline material according to claim 1, and
 (ii) recovering said granulated material.

13. A method for manufacturing a solid product, said method comprising the steps of:
 (i) grounding the glassy-crystalline material according to claim 1;
 (ii) mixing said material with sintering aids;
 (iii) processing said material into a slurry;
 (iv) applying said slurry onto a polyurethane sponge;
 (v) sintering said sponge in at least one sintering stage; and
 (vi) recovering a solid product, said product comprising apatite and calcium zirconium phosphate as main crystalline components.

14. A method for manufacturing ceramic bodies or ceramic sheets, said method comprises
 (i) grinding the glassy-crystalline material according to claim 1;
 (ii) adding sintering aids to form a slurry;
 (iii) processing said slurry into a body or sheet;
 (iv) heating said body or sheet; and
 (v) recovering a product, wherein said product comprises an open-pore structure.

* * * * *